United States Patent [19]

Craig

[11] 4,122,847

[45] Oct. 31, 1978

[54] PROTECTIVE EYE SHIELD FOR SURGICAL PATIENTS

[76] Inventor: Robert G. Craig, 1915 Summit Ridge Dr., Escondido, Calif. 92025

[21] Appl. No.: 818,291

[22] Filed: Jul. 25, 1977

Related U.S. Application Data

[63] Continuation of Ser. No. 620,814, Oct. 8, 1975, abandoned.

[51] Int. Cl.$^2$ .............................................. A61F 9/04
[52] U.S. Cl. ..................................... 128/132 R; 2/15
[58] Field of Search ............ 128/132 R, 145 A; 2/15, 2/12, 427, 428, 431–441; 351/41, 43, 110, 144, 150, 140

[56] References Cited

U.S. PATENT DOCUMENTS

| 583,590 | 6/1897 | Bennett | 2/452 |
|---|---|---|---|
| 2,149,514 | 3/1939 | Fischer | 2/436 |
| 2,243,982 | 6/1941 | Seeley | 2/12 |
| 2,387,851 | 10/1945 | Lonn et al. | 2/441 |
| 2,430,881 | 11/1947 | Lehmberg | 2/437 |
| 2,568,316 | 9/1951 | Brown | 2/428 |
| 3,092,103 | 6/1963 | Mower | 128/132 R |
| 3,333,586 | 8/1967 | Bellis et al. | 2/427 X |
| 3,351,061 | 11/1967 | Nolan | 128/283 |
| 3,526,449 | 9/1970 | Bolle et al. | 351/41 |
| 3,758,202 | 9/1973 | Chuwga | 351/41 |
| 3,952,331 | 4/1976 | Melville | 2/431 |

FOREIGN PATENT DOCUMENTS

| 639,346 | 12/1936 | Fed. Rep. of Germany | 2/439 |
|---|---|---|---|
| 575,231 | 5/1936 | Switzerland | 2/427 |

*Primary Examiner*—Henry J. Recla
*Attorney, Agent, or Firm*—Seiler & Quirk

[57] ABSTRACT

A protective eye shield for patients during surgery comprises a flexible face mask, preferably soft, foamed plastic, for lying across the patient's brow or forehead, around the eyes and upper cheeks, and across the nose bridge, and having a pair of openings covered by transparent eye covers secured to the mask member, and a contact adhesive inner surface for securing the periphery of the mask to the face of the patient.

2 Claims, 5 Drawing Figures

PROTECTIVE EYE SHIELD FOR SURGICAL PATIENTS

This is a continuation of application Ser. No. 620,814 filed Oct. 8, 1975 now abandoned.

BACKGROUND OF THE INVENTION

During surgical procedures, especially where general anesthesia is used, the patient is often lying on his or her back, with the eyes and face exposed. The patient's eyelids may not be fully closed during the surgery, and, in a number of procedures, it is desirable to have the eyelids open in order to observe the eyes in monitoring the effects of anesthesia. However, it is not uncommon for the patient to sustain some eye injury during the surgery from the various apparatus and monitoring devices located near the head and back. The most common such injury is corneal abrasion, which may be painful, and, if not treated, may lead to serious eye infection and possible permanent corneal injury. The abrasive eye injury may be caused by instruments, fingers, arms, dressings, face masks, apparatus tubing or other materials inadvertently contacting the delicate surface of the eye. In other cases, various liquids utilized during surgery may inadvertently be dripped into the eyes, or blood may flow into the eyes, particularly during a tonsillectomy and the like, all of which may be very injurious or toxic to the delicate eye membranes. It is to the elimination of these problems that the present invention is directed, whereby the eyes are protected both from contact by abrasion causing materials as well as from liquids or other foreign objects which may contact the eye thereby causing injury.

OBJECT AND SUMMARY OF THE INVENTION

It is an object of the present invention to provide a lightweight, inexpensive, and disposable shield for use on patients during general anesthetic surgery. It is another object to provide an efficient eye shield which may be secured substantially entirely around the eyes whereby fluid drainage into the eyes is prevented. It is still another object to provide an eye shield having transparent eye covers through which the condition of the patient's eyes may be observed during a surgical procedure under general anesthesia. These objects are met by the device of the present invention, comprising a base member in the form of a flexible face mask which may be secured substantially entirely around the patient's eyes, across the forehead, temples, upper cheeks and nose bridge, and which includes transparent eye covers through which the patient's eyes may be observed, which covers are secured to the mask base. Such features of the device in achieving the aforesaid as well as other objects and further characteristics of the invention will be evident from the following detailed description.

DETAILED DESCRIPTION OF THE INVENTION

Figure 1:
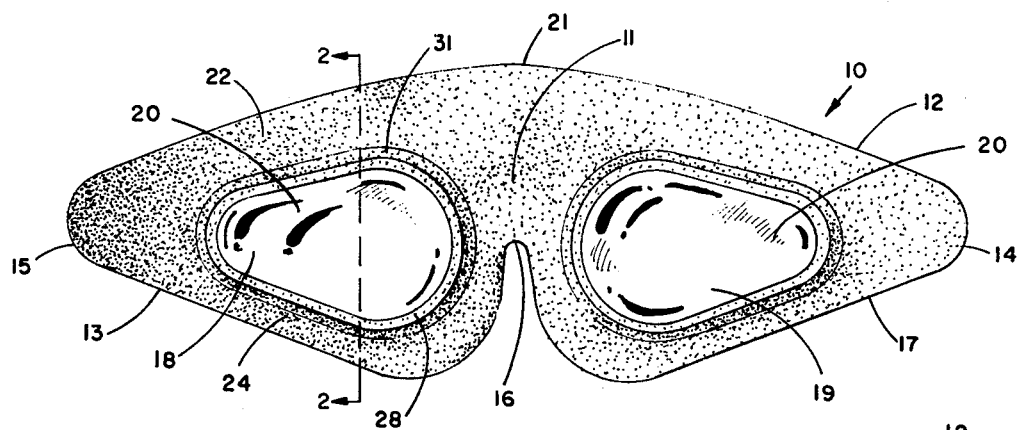
FIG. 1 is a view illustrating the eye shield of the invention.
Figure 4:
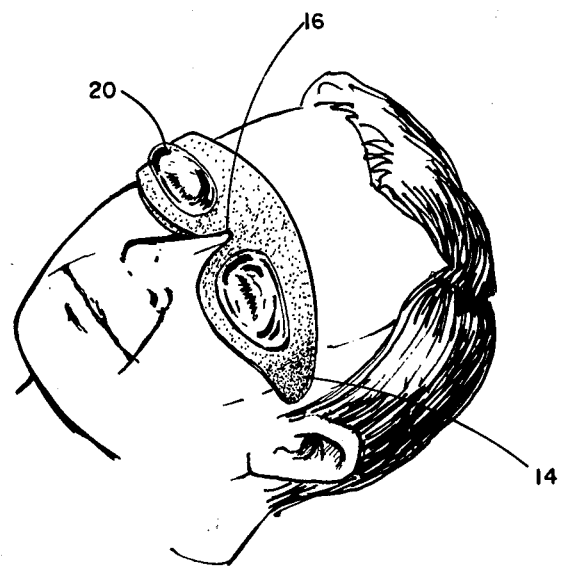
FIG. 4 is a view showing the device of FIG. 1 secured on a patient.

As is shown in FIG. 1, the protective eye shield 10 of the invention comprises a face mask member 12 having two substantially identical opposite portions 13 and 17, respectively, joined by a bridge portion 11. The mask member acts as a base for the eye cover and has an opening 17 and 18 directly over each eye. Preferably, at each end of the face mask member there are enlarged portions 14 and 15 for overlying the patient's temples as shown in FIG. 4. The mask is also preferably provided with a notch 16 extending upwardly into bridge 11 between openings 18 and 19 and through which the upper portion of the patient's nose extends with the mask secured. The width of the notch is not so important nor is its length into the bridge so long as it provides sufficient space for the nose without rubbing or otherwise causing irritation. In a preferred mask, an enlarged upper portion 21 is provided to overlie a larger portion of the patient's forehead. Thus, the enlarged area affords more surface for being secured to the relatively smooth flat forehead above the eyebrows and nose bridge.

Figure 2:
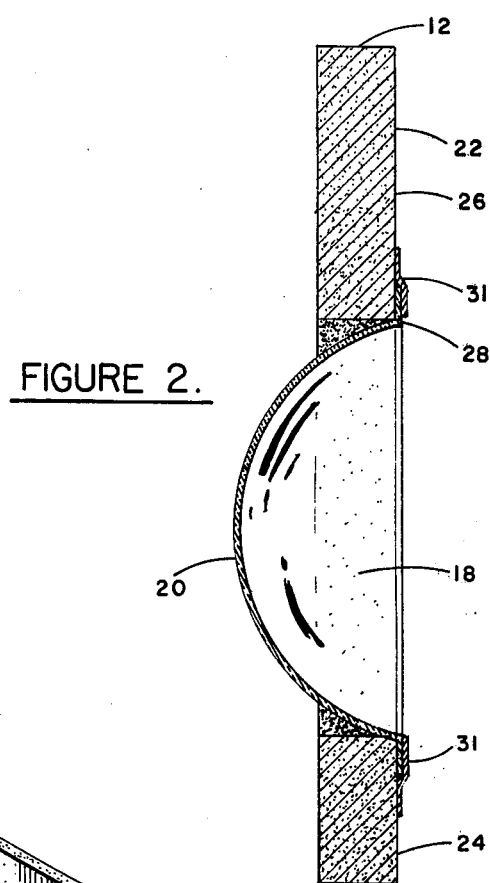
FIG. 2 is an enlarged sectional view taken along lines 2—2 of FIG. 1.

FIG. 2 is an enlarged cross-section illustrating a preferred eye shield embodiment wherein the face mask member 12 comprises a flexible, soft, sponge-like material, such as foamed or expanded synthetic resins, which are soft and resilient. Particularly useful are the flexible polyurethane (polyether), polyethylene, and polystyrene foams. Such materials are lightweight, inexpensive, flexible, and relatively soft thereby providing excellent mask base material for being comfortably secured to a patient. One of the openings, 18, is shown between upper and lower mask portions 22 and 24, respectively, which directly overlies the patient's eyes.

Covering each opening 18 and 19 is a transparent cover 20 which may be secured in any suitable way to the mask member. For example, it may be bonded to the outer mask surface utilizing any suitable bonding technique, such as adhesive, or it may be similarly secured to the inner surface as illustrated in FIG. 2. For example, an adhesive or other bonding agent is used between the flange 28 and the inner (or outer) mask surface to secure the eye cover. The cover should preferably be convex in shape, protruding outwardly to allow room for movement of the patient's eyelids and eyelashes. The covers preferably comprise a thin, transparent plastic cup having a flange 28 therearound for being secured to the mask surface as illustrated in FIG. 2.

In the embodiment shown, a tape 31 is optionally used around the edge of the eye cover 20. The tape is secured around the periphery of the flange 28 and to the inner mask surface thus overlying the cup edge. The purpose of the tape is to prevent a sharp surface of the eye cover from being exposed to the patient. This is particularly advantageous should the cover become cracked or split at the cup edge thereby presenting a sharp corner of material which could cause injury to the skin or eyes of the patient. The tape would prevent such injury as well as further securing the eye cover to the mask. The tape may, but need not be transparent and preferably has a contact adhesive on both surfaces for bonding it to the mask and to the patient.

The type of plastic used for the transparent covers is preferably somewhat hard or rigid. Flexibility is not a requirement where the cup is of a design as shown in FIGS. 1 and 2. Instead, some rigidity is important so that the cup is able to withstand pressure from materials or the like which may fall on the mask during the surgical procedure. Preferred materials are the cellulosics such as cellulose acetate, cellulose acetate butyrate, cellulose acetate propionate, polypropylene, polyethylene, and polyvinyl chloride. Acrylic resins such as Lucite or Plexiglas may be used as may any plastic which is transparent or translucent and lightweight, and rigid enough to withstand at least moderate pressure without collapsing.

Again, observing FIG. 4, the face mask member is designed to be secured to the patient's face, substantially entirely around the patient's eyes, including the forehead or brow, temples, and nose bridge. For this purpose, it is necessary to utilize a means for securing the shield to the patient's face. Most suitably, a contact adhesive is coated on inner surface 26 of the flexible face mask member 12, at least around the periphery so as to fully secure the mask to the patient's face by applying slight pressure. Alternatively, an adhesive backed tape may be applied to the mask surface. With the contact adhesive around the periphery of the inner surface of the mask, it will be secured to prevent liquid from leaking between the skin and mask and into the eye. However, even more preferably, the adhesive is present entirely around the inner surface of the mask member so that any areas of contact with the skin will cause the mask to adhere thereto, thereby even further positively securing the device to the patient's face and avoiding problems of liquid entry. Any contact adhesive may be used on the inner mask surface, preferably an FDA approved medical grade adhesive. The adhesive may be in the form of a composition applied to the mask surface or a layer of skin of tape having adhesive on both sides.

Figure 3:
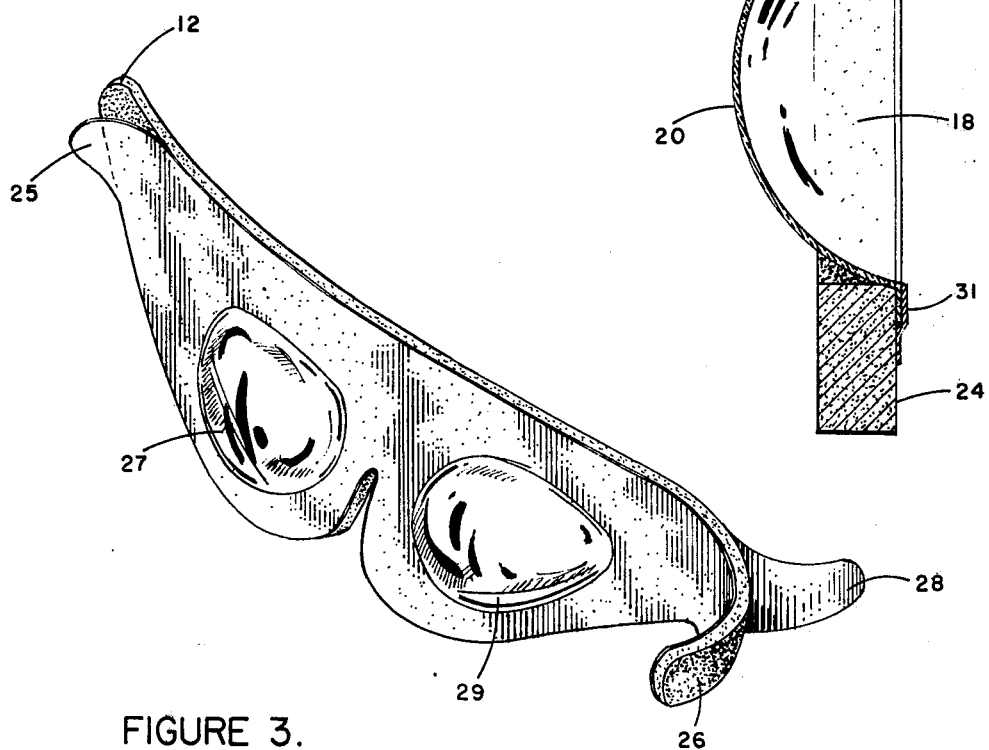
FIG. 3 is a perspective view of another eye shield embodiment of the invention.

Another mask embodiment is illustrated in FIG. 3 in which the front of the mask comprises a transparent sheet secured to the mask base. Transparent sheet 25, shown peeled back for the purpose of illustration, is bonded to the exterior surface of the flexible foam base member 12 and which sheet includes integral eye covers 27 and 29. In such an embodiment the eye covers are convex protruberances or cups formed in the transparent plastic sheet 25 made of one of the previously mentioned eye cup materials. However, in this form, the transparent plastic sheet should be a material flexible enough so that the mask can be formed to the patient's face including the temples at the enlarged end areas 14 as illustrated in FIG. 4. If the transparent plastic sheet were too rigid, although the mask and sheet may be pre-formed to generally fit over the areas of the patient's face, there may be problems in keeping the enlarged end portions 14 and 15 secured against the patient's temples. Thus, a plastic sheet having a significant "memory" property may be used if it is subjected to a pre-forming or molding process with the end areas angled to lie flat against the temples. FIG. 3 further shows the inner surface 26 which is coated with a contact adhesive and covered with a protective liner 28 to prevent drying or other deterioration of the adhesive prior to use. The liner will normally be peeled off immediately before the shield is secured on a patient. For this purpose, a paper or similar material treated so as to be easily removed from the adhesive without otherwise deteriorating the adhesive properties is used.

Figure 5:
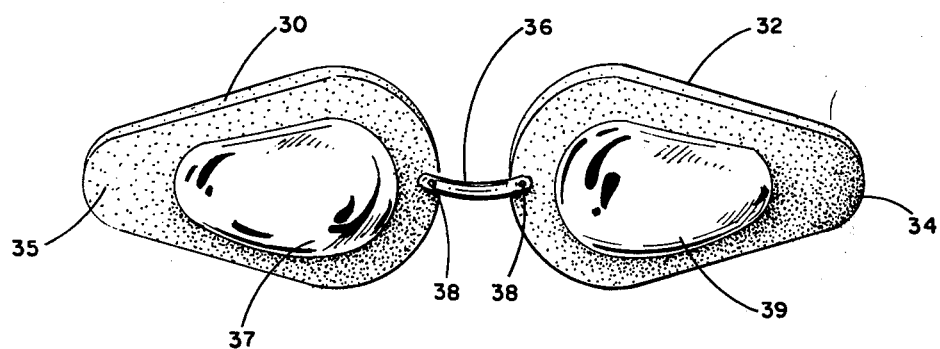
FIG. 5 is a view showing another embodiment of an eye shield according to the invention.

FIG. 5 illustrates still another embodiment of an eye shield of the invention. In the device shown, there are a pair of eye cover members 30 and 32, joined by a bridge member 36, the latter being a ductile or malleable material such as aluminum or a similar soft metal or alloy. The cover members 30 and 32 are preferably a flexible foamed plastic each having an opening over which are secured transparent cups 37 and 39, as previously described. Again, these transparent cups may be secured in any suitable way, either to the interior or exterior surfaces of the eye cover members 30 and 32 as previously described. These cover members also include enlarged sections 34 and 35 for being secured to and overlying the temples of the patient as previously described. The interior surface of the covers are also coated with the contact adhesive for securing the device to the patient's face.

The malleable or ductile bridge member 36 may be formed to any desired shape to fit a particular patient. The device is simply placed on the patient's face and the bridge formed by use of one's fingers to either flatten or bow the bridge to achieve the desired space and separation between the cover members. The bridge 36 may be secured to the cover members by the use of enlarged tabs or nipples 38 which are integral with and part of the cover members and extend through small openings at each end of the bridge. Other alternative means for securing the bridge to these cover members such as rivets or adhesives and the like may be used.

In using the eye shield and regardless of the embodiment used, the surgeon or anesthesiologist simply first peels off the protective lining covering the inner adhesive surface and places the eye shield on the patient's face, centering it properly so that the nose extends through the notch and the openings and eye covers are properly located over the patient's eyes. Light pressure is then exerted around the exterior surface of the eye shield, by pressing the soft, flexible foam mask member against the patient's forehead, around the eyes, temples and nose bridge so that it is firmly secured. The device remains on the patient during the surgery and thereafter is simply peeled off and discarded. Naturally, the adhesive used on the inner surface of the mask for securing it to the patient's face must properly prevent any substantial openings therebetween through which fluid could leak into the patient's eyes, but should not be so tacky or stiff as to be difficult to remove. If the adhesive is too sticky or tacky, it may pull eyebrows and skin and otherwise cause discomfort to the patient during removal which is not satisfactory.

The limitations described herein as well as other embodiments and modifications of the eye shield within the purview of the invention will be evident to those skilled in the art.

I claim:

1. A protective eye shield for a surgical patient comprising:

a unitary flexible, soft and relatively thick, foamed, plastic blank means of substantially uniform thickness, having a substantially flat surface and shaped for covering a patient's lower forehead, across and beneath the eyes, and across the upper nose bridge, and having a pair of opposite openings over the eyes, said flat inner surface having a contact adhesive entirely around the peripheral portion thereof for securing the eye shield to the patient, a pair of thin, transparent, plastic covers overlying said openings, each cover having a flange terminating in a peripheral edge extending therearound, and which flange is secured to the inner mask surface around said openings, and tape, relatively thin as compared to the thickness of said foamed, plastic blank means, secured to said inner mask surface and substantially entirely around said flange to overlie said peripheral cover edge, whereby a patient is protected from said edge by said tape.

2. During a general surgical procedure, a method of preventing injury to a patient's eyes comprising placing a protective eye shield of claim 1 on said patient's face so that the patient's eyes are observable through said covers and openings, and exerting pressure around the exterior shield surface by pressing the blank means against the patient's forehead, around the eyes, temples and nose bridge to secure said adhesive to the patient's skin.

* * * * *